United States Patent

Kawesch

[11] Patent Number: 6,019,754
[45] Date of Patent: Feb. 1, 2000

[54] METHOD AND APPARATUS FOR IMPROVING LASIK FLAP ADHERENCE

[76] Inventor: Glenn Kawesch, 3916 Santa Nella Pl., San Diego, Calif. 92130

[21] Appl. No.: 09/182,334

[22] Filed: Oct. 29, 1998

[51] Int. Cl.[7] .............. A61N 5/06; A61B 17/36
[52] U.S. Cl. .................. 606/4
[58] Field of Search .............. 606/4, 5, 6, 10, 606/11, 12, 17; 623/107, 4, 5

[56] References Cited

U.S. PATENT DOCUMENTS

| | | | |
|---|---|---|---|
| 3,982,541 | 9/1976 | L'Esperance, Jr. | 128/303.1 |
| 4,550,713 | 11/1985 | Hyman | 128/1 R |
| 4,559,942 | 12/1985 | Eisenberg | 128/303 |
| 4,903,695 | 2/1990 | Warner et al. | 606/4 |
| 5,009,660 | 4/1991 | Clapham | 606/166 |
| 5,092,863 | 3/1992 | Schanzlin | 606/5 |
| 5,108,412 | 4/1992 | Krumeich et al. | 606/4 |
| 5,139,518 | 8/1992 | White | 623/5 |
| 5,230,347 | 7/1993 | Weinstein et al. | 128/740 |
| 5,269,812 | 12/1993 | White | 623/5 |
| 5,312,330 | 5/1994 | Klopotek | 604/49 |
| 5,533,997 | 7/1996 | Ruiz | 606/5 |
| 5,586,980 | 12/1996 | Kremer et al. | 606/4 |
| 5,616,139 | 4/1997 | Okamoto | 606/4 |
| 5,620,435 | 4/1997 | Belkin et al. | 606/4 |
| 5,658,303 | 8/1997 | Koepnick | 606/166 |
| 5,697,945 | 12/1997 | Kritzinger et al. | 606/161 |
| 5,722,971 | 3/1998 | Peyman | 606/2 |
| 5,728,041 | 3/1998 | Fowler, Jr. | 600/21 |
| 5,752,967 | 5/1998 | Kritzinger et al. | 606/166 |
| 5,807,380 | 9/1998 | Dishler | 606/4 |
| 5,919,185 | 7/1999 | Peyman | 606/4 |

*Primary Examiner*—Linda C. M. Dvorak
*Assistant Examiner*—Sonya Harris-Ogugua
*Attorney, Agent, or Firm*—Bourque & Associates, P.A.

[57] ABSTRACT

A method and apparatus, which provides improved conditioning and adherence of a resected corneal flap into its original position on the eye following the laser ablation step of LASIK vision correction surgery is disclosed. The method comprises resecting at least a portion of at least one of a person's eyes to expose an inner layer of said cornea, which is sculpted using radiation from a laser beam to produce a desired corneal topography. After the desired topography is achieved, the corneal flap is floated back into its proper position in a sterile solution and to remove any debris associated with the sculpting step from the patient's eye. After the corneal flap is repositioned, a flap drying apparatus is used to dry the repositioned corneal flap by applying filtered, compressed air at a flow rate substantially between zero and 2.5 liters per minute at an appropriate pressure to draw the sterile solution away from the corneal flap/inner corneal layer interface without disturbing the positioned or alignment of the repositioned corneal flap. An ophthalmic surgeon observes the corneal flap using a microscope while applying the filtered, compressed air to the corneal flap, for substantially between 15 and 30 seconds, paying particular attention to a gutter area surrounding corneal flap. The surgeon terminates the application of the filtered, compressed air when the gutter area is observed to be substantially dry.

13 Claims, 2 Drawing Sheets

METHOD AND APPARATUS FOR IMPROVING LASIK FLAP ADHERENCE

FIELD OF THE INVENTION

The present invention relates to the field of ophthalmic surgery. Specifically, the invention is directed to a method and apparatus for improving the adherence of a corneal flap once it is repositioned on the eye during LASIK vision correction surgery. The method includes floating the corneal flap into its original position in a sterile solution and applying filtered, low pressure, compressed air to the repositioned flap in a controlled manner so as to dry the flap in position, which improves flap adherence and speeds up the surgical procedure.

BACKGROUND OF THE INVENTION

Throughout history, mankind has experimented with various means of improving vision using external devices and instruments. While glasses and contact lenses do provide many people a reasonable quality of life, they do have limitations. For example, for many lifestyles, glasses can be inconvenient. And, for some people they do not give the quality of vision desired.

Contact lenses have addressed some of the inconveniences of glasses. The apparent invisibility of contact lenses has satisfied those who were self-conscious about wearing eyeglasses. In addition, contact lenses have allowed people to engage in activities that were previously either prohibited or difficult to engage in while wearing glasses, such as certain athletic endeavors. Nonetheless, wearing contact lenses does come with a price. In addition to the price of lenses, contact lens wearers must devote a considerable amount of time in maintaining their lenses. In addition, there still are limitations as to the types of activities one can participate in while wearing contact lenses, such as swimming or other water sports where contact lenses can be floated out of the eye. Lastly, long term contact lens wearers may develop an intolerance to wearing lenses or develop long term eye damage.

As a result of the limitations of glasses and contact lenses, ophthalmologists have developed a number of surgical procedures, as which modify the eye itself—to correct the actual cause of poor vision in the first place. One early form of vision correction surgery was radial keratotomy (RK). RK is basically a surgical operation, which can improve myopia (nearsightedness) by flattening the curve of the cornea over the pupil. A surgeon makes several radial incisions in the cornea with a scalpel. These cuts are fairly deep and are designed to cause the central cornea to relax or flatten and the peripheral cornea to steepen, which reduces the dome of the central cornea. This results in effectively modifying the focal length of the eye's lens, allowing light to focus on the retina.

However, RK does have serious shortcomings. First, and perhaps most significant, is that the radial cuts in the cornea are required to be fairly deep. In fact, sometimes these cuts extend up to 90% of the thickness of the cornea. As can be appreciated, the depth of these cuts seriously weakens the cornea, which frequently leads to progressive flattening of the cornea and increasing farsightedness, (the opposite of the nearsightedness the RK procedure was tailored to correct). In addition, RK can only be used to correct low amounts of myopia. Furthermore, it cannot correct hyperopia (farsightedness).

A more recent development in vision correction is a procedure called photorefractive keratectomy (PRK). As with RK, PRK modifies the shape of the cornea to correct vision. However, the process is very different and provides significant improvements in patient risk and correction capabilities. Instead of making SE radial cuts in the cornea with a scalpel, PRK uses an excimer laser to sculpt an area 5 to 9 millimeters in diameter on the surface of the eye. This process removes only 5 to 10% of the thickness of the cornea in mild to moderate myopia and only up to 30% for extreme myopia. The major benefit of PRK is that the integrity and strength of the corneal dome is retained. The excimer laser is set at a wavelength of 193 nm, which will remove a microscopic corneal cell layer without damaging adjoining cells. This allows an ophthalmic surgeon to make extremely accurate and specific modifications to the cornea with little trauma to the eye.

The ability to sculpt, rather than cut, opens up the area for treating a number of vision conditions, including hyperopia and astigmatism.

An even more recent development is a procedure known as LASIK. The LASIK procedure is a hybrid procedure, which involves both a surgical cutting and laser sculpting of the cornea. FIG. 1 shows a normal eye before any type of vision correction surgery is performed. Eye 10 includes cornea 12, which includes an outer layer called the epithelium 14. The epithelium is a protective outer layer of the cornea. With PRK, the epithelium is sculpted along with the remainder of the cornea. However, it is essentially unaltered with the LASIK procedure. The first step in the LASIK procedure is to slice the cornea from the side to produce a corneal flap 16 including the epithelium 14. (See FIG. 2) The flap is cut using a device called a microkeratome. A part of the microkeratome flattens the cornea during the slice so as to create a corneal flap of uniform thickness. The slice is completed before a complete disk is created, which results in a corneal flap 16 of uniform thickness with hinge 18 at one edge thereof. The surgeon then rolls the flap back to expose an inner layer 20 of the cornea 12. With the flap folded back, the surgeon performs the refractive correction on the inner layer 20 of the cornea using an excimer laser in a manner similar to PRK. When the corneal sculpting is complete, the flap is repositioned into its original position and the procedure is complete. The eye has a natural suction facility that retains the flap firmly in place at this time. However, care must be taken by the doctor to insure an excellent fit when repositioning the flap. It is this critical aspect of the LASIK procedure to which the present invention is directed.

Since this portion of the LASIK procedure is critical to the resultant improvement in eyesight, many apparatuses and methods have been developed in order to aid in the precise repositioning and adherence of the corneal flap. Of particular importance is U.S. Pat. No. 5,533,997, which issued to Ruiz on Jul. 9, 1996. The '997 Patent discloses a LASIK procedure especially tailored to correct presbyopia. The '997 Patent discloses that after the laser ablation step of the LASIK procedure is accomplished, the ablated layer of the cornea is exhaustively cleaned using a balanced saline solution, a brush and aspiration in order to assure that the interface is free from impurities, epithelial cells or foreign particles. (Col. 3, lines 38–42) The '997 Patent further discloses that thereafter, the flap is replaced in the bed, adequately oriented in order to avoid altering its natural position. The edges of the flap are then dried using air for several seconds to obtain adherence of the flap. However, the drying step disclosed in the '997 Patent is not controlled. Accordingly, this procedure can result in the dislocation of the corneal flap caused by the air used to dry its edges. In addition, since the bonding of the flap is not controlled, it is tested or verified using tweezers. (Col. 6, lines 14–15). If the flap is not adequately bonded, then the tweezers could reposition the flap, which would require an additional positioning and drying step. The adherence verification method could also lead to damage of the corneal flap caused by the tweezers themselves.

Accordingly, the disclosed invention provides a method and apparatus which can be used in drying a corneal flap during the LASIK procedure, which results in controlled drying under the observation of an ophthalmic surgeon until adequate drying and flap adherence is observed.

SUMMARY OF THE INVENTION

The present invention provides a method and apparatus, which provides improved positioning and adherence of a resected corneal flap into its original position on the eye following the laser ablation step in LASIK vision correction surgery. The method comprises resecting at least a portion of a cornea of at least one of a person's eyes to expose an inner layer of said cornea. Once the inner layer of the cornea is exposed, it is sculpted using radiation from a laser beam to produce a desired corneal topography. After the desired topography is achieved, the corneal flap is floated back into position in a sterile solution to insure that the corneal flap interfaces the sculpted inner corneal layer in a correct position corresponding substantially to its original position before the resection and sculpting steps. The floating step also aids in removing any debris associated with the sculpting step from the patient's eye. After the corneal flap is repositioned, it is dried using a flap drying apparatus of the present invention, which applies filtered, compressed air at an adjustable flow rate ranging from zero to 2.5 liters per minute at an appropriate pressure to draw the sterile solution away from the corneal flap/inner corneal layer interface without disturbing the positioned or alignment of the repositioned corneal flap. During the application of the filtered, compressed air, an ophthalmic surgeon observes the corneal flap using a microscope, paying particular attention to a gutter area surrounding the corneal flap, intermediate the flap and the portion of the person's cornea that remained intact during the corrective surgical procedure. Finally, the drying step is completed when the gutter area is observed to be substantially dry. The drying step takes substantially between 15 and 30 seconds and assures adequate corneal flap adherence without the need to perform mechanical testing upon the corneal flap.

The invention also provides an apparatus for surgical vision correction. The apparatus includes a means for resecting at least a portion of a cornea of an eye to expose an inner layer of the cornea. Also included is a laser apparatus for ablating the exposed inner layer of the cornea to produce a desired corneal topography, a source of sterile solution for floating the resected portion of the cornea back into its original position on the eye following the laser ablation, a corneal flap dryer for drying the eye and a microscope for viewing the repositioned portion of the cornea to ensure proper orientation and smoothness and for viewing the patient's cornea during the drying process. The corneal flap dryer comprises a source of compressed air and volume and pressure regulators to control the flow of the compressed air at a variable rate ranging from zero to substantially 2.5 liters per minute an appropriate pressure to assure adequate corneal flap drying and adherence in substantially between 15 and 30 seconds without risking the dislocation of the corneal flap during the drying process.

DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENT

Figure 1:
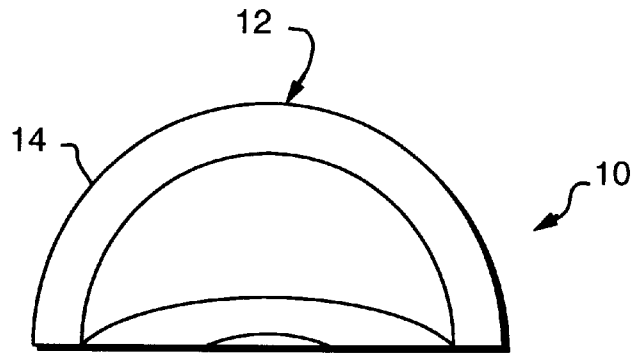
FIG. 1 is a side view of a typical eye before a LASIK vision corrective procedure is performed.
Figure 2:
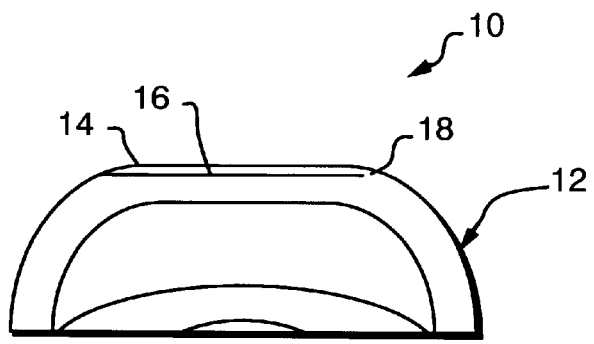
FIG. 2 is a side view of the eye of FIG. 1 showing a slice of the cornea performed using a microkeratome to produce a corneal flap of a uniform thickness.
Figure 3:
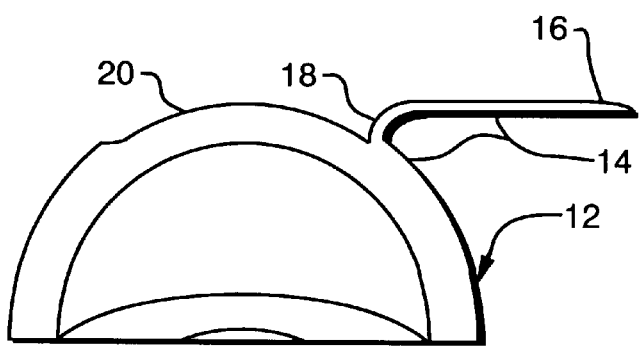
FIG. 3 is a side view of the eye of FIG. 2 showing the corneal flap folded back to expose the inner layer of the cornea.
Figure 4:
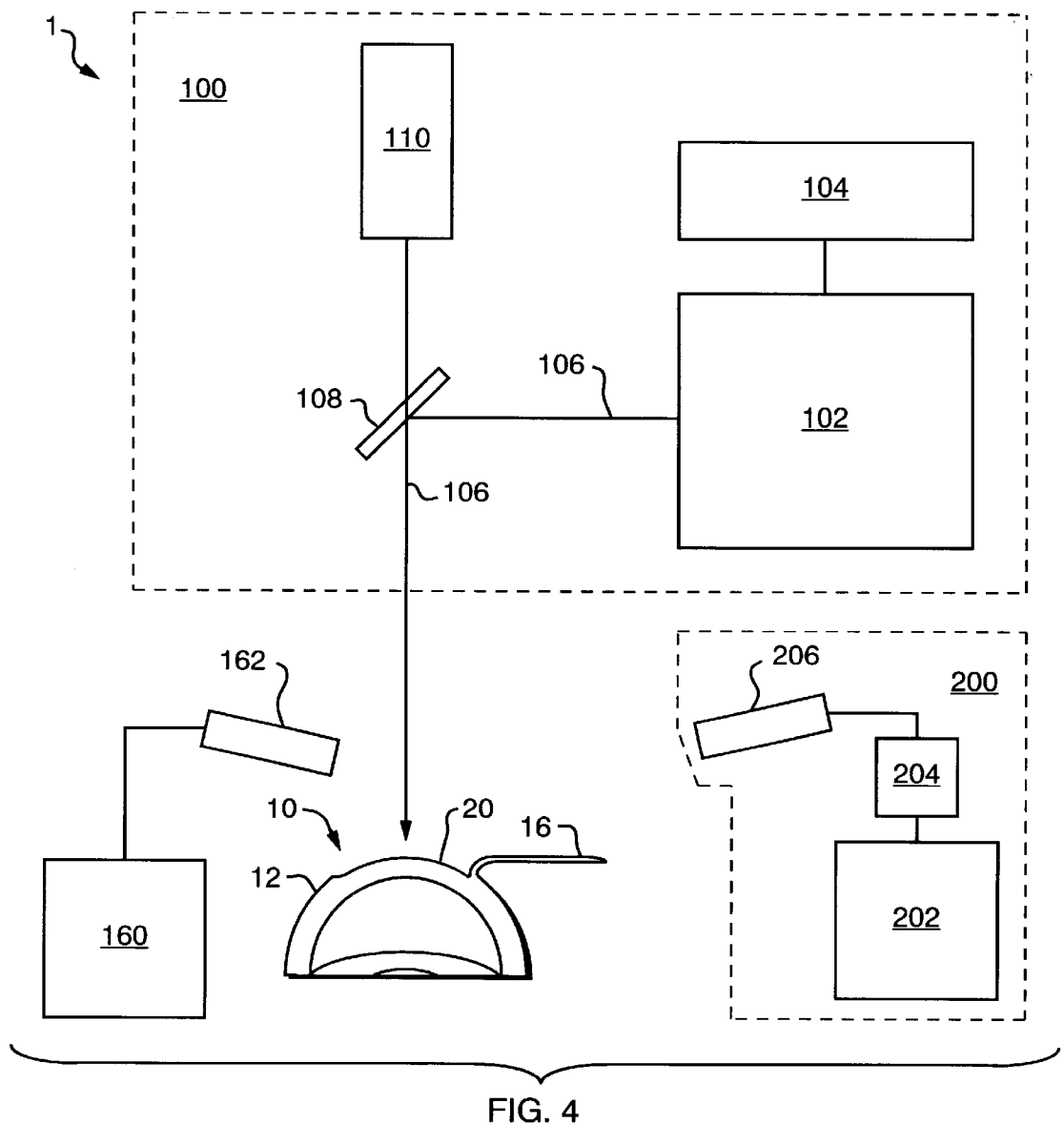
FIG. 4 is a schematic block diagram of an apparatus according to the present invention during the laser ablation portion of a LASIK procedure.

Turning now to the figures and in particular FIG. 4, an apparatus 1, according to the present invention is shown and includes a computer controlled laser-based automatic corneal shaper 100, which, in one preferred embodiment is a VISX ophthalmic surgical laser apparatus. Corneal shaper 100 includes an excimer laser 102 which is controlled by computer 104. Laser beam 106, which is generated by excimer laser 102 is directed onto eye 10 and, in particular, an exposed inner layer 20 of cornea 12. The direction of laser beam 106 is accomplished using a beam splitter/mirror 108. Also included, either as in integral component of corneal shaper 100 or as an independent apparatus is microscope 110, through which an ophthalmic surgeon monitors the by operation of apparatus 100 through beam splitter/mirror 108.

Using local anesthesia, a patient's eye is fixed by a fixation ring such as the one disclosed in U.S. Pat. No. 5,133,726 which issued to Ruiz on Jul. 28, 1992.

Once the eye is fixed, a keratectomy is performed using a device called a microkeratome in the manner discussed earlier. The keratectomy may be partial, which means that the above-mentioned corneal flap technique is used. This technique allows an end portion of the corneal disk to remain attached to the corneal base, thereby facilitating the repositioning of the corneal flap once the corneal is ablated using the excimer laser. When the flap is retracted, an inner layer of the cornea is exposed, which is the preferred tissue on which to practice laser ablation in order to sculpt the cornea to produce a desired corneal topography. In this way, the superficial layers of the cornea including the epithelium remain untouched. This results in improved healing and avoids inaccuracies in post-operative correction and regression.

Using an excimer laser, set at a wavelength of approximately 193 nm, a microscopic corneal cell layer can be ablated without damaging any adjoining cells. This allows the ophthalmic surgeon to make extremely accurate and specific modifications to the cornea with little trauma to the eye. Using a VISX apparatus, for example, which controls the excimer laser 102 using a computer 104, extremely accurate and precise corneal topographies can be produced with very little risk of error.

After the desired corneal topography is achieved, the surgeon thoroughly cleans the sculpted layer of the cornea by flushing the eye with a sterile, balanced saline solution provided via dispensing valve 162 from a solution source 160. The flushing step assures that the corneal flap/inner corneal layer interface is free from impurities, epithelial cells and foreign particles. The exposed, back side of the corneal flap is also thoroughly cleaned to insure the corneal flap interface remains clean. Thereafter, the surgeon repositions the flap over the sculpted cornea. The surgeon views this step of the procedure using microscope 110 through beam splitter/mirror 108 to ensure that the corneal flap is properly oriented and is adequately smooth so as to avoid the creation of vision complications.

All of the above identified equipment and methods are well know to those skilled in the ophthalmic surgery art. However, the disclosed apparatus and method differs from the prior art at this point in the procedure. Once the surgeon cleans the cornea and ensures that the corneal flap 16 is properly repositioned, the surgeon uses a corneal flap drying device 200, such as a Kawesch flap dryer, in order to dry the corneal flap in position to facilitate its adherence to the newly sculpted inner layer of the cornea. The corneal flap drying device 200 may be integrated into a complete laser-based vision surgery apparatus or it may be a separate, retrofit unit that can be added to and used in conjunction with existing laser surgery system. In either embodiment, the use of the disclosed corneal flap drying device minimizes waiting time after floating the flap into position to substantially between 15 and 30 seconds and insures excellent flap adherence. The Kawesch flap dryer 200 includes a source of filtered, compressed air 202, a pressure regulator 204 and a manually operated, flow restricting valve 206. Valve 206 is opened by a surgeon and is manipulated to direct a very low flow of filtered, compressed air over the repositioned corneal flap in order to draw the fluid out of the cornea/flap interface. The flow restricting valve 206 is selected so as to provide a variable filtered air flow rate ranging from zero to substantially 2.5 liters per minute at an appropriate pressure, which is regulated by the pressure regulator 204. The limited flow rate and associated pressure are required to provide sufficient air flow for convective drying while, at the same time, minimize the possibility of blowing the repositioned flap out of its proper position.

Figure 5:
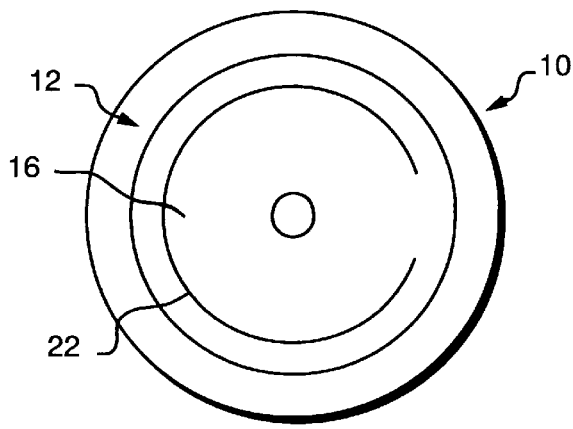
FIG. 5 is a top view of a patient's eye following corneal flap repositioning showing a gutter area substantially circumferentially surrounding the repositioned corneal flap.

While the surgeon is operating valve 206 and applying filtered, compressed air over the flap, the surgeon views the drying process through a microscope 110. In addition to insuring that the repositioned flap does not move during the drying process, the surgeon pays particular attention to a gutter area 22 (FIG. 5), which substantially circumferentially surrounds the repositioned corneal flap. This gutter, which defines the edge of the cornea/flap interface appears wet following the flushing and floating of the corneal flap back into its position on the eye. However, due to convective drying, when the low flow, filtered compressed air is applied from flap dryer 200 onto the flap, the fluid beneath the repositioned flap will be drawn out of the cornea/flap interface. When the surgeon observes that the gutter area is substantially dry, the surgeon terminates applying the compressed air onto the flap since it is at this point that an excellent flap adherence is accomplished. This part of the procedure typically takes between 15 and 30 seconds.

The Kawesch flap dryer has been used on a number of patients, all of whom seem to see better upon sitting up following the procedure than those whose corneal flaps have not been dried following the procedure. In addition, none of the test patients have experienced greater than a 0.75 diopter astigmatism on day 1, which indicates that the Kawesch flap dryer does not adversely affect the position or smoothness of the repositioned flap. A further advantage of the drying technique is that patients who experience some bleeding from neo-vascularization at the flap edge do not experience a substantial amount of blood flowing beneath the corneal flap due to the rapid flap adherence.

Accordingly, the disclosed apparatus and method results in faster and more secure flap adherence than LASIK procedures that do not utilize a drying apparatus or method. In addition, the controlled manner in which the Kawesch flap dryer allows a surgeon to expose the repositioned flap to a flow of compressed air results in substantially fewer complications resulting from flap movement caused by uncontrolled, rapid drying methods.

Modifications and substitutions by one of ordinary skill in the art are considered to be within the scope of the present invention which is not to be limited except by the claims which follow.

What is claimed is:

1. A method of permanently correcting a person's vision comprising the steps of: resecting a least a portion of a cornea of at least one of said person's eyes to expose an inner layer of said cornea; sculpting said inner layer of said cornea using radiation from a laser beam to produce a desired corneal topography; floating said corneal flap back into position in a sterile solution to ensure said corneal flap interfaces said sculpted inner corneal layer in a correct position and to remove any debris associated with said sculpting step; applying filtered compressed air at a flow rate substantially between zero and 2.5 liters per minute to draw said sterile solution away from the corneal flap/inner corneal layer interface; observing said application of filtered compressed air using a microscope, paying particular attention to a gutter area surrounding said corneal flap intermediate said corneal flap and said person's cornea that remained intact during said method; and terminating said step of drying when said gutter area is observed to be substantially dry.

2. The method of claim 1, wherein said step of applying filtered, compressed air to said corneal flap is performed substantially between 15 and 30 seconds.

3. The method of claim 1, wherein said resecting step comprises, resecting said cornea such that a portion of said cornea remains intact and said corneal flap is folded back to expose said inner corneal layer.

4. The method of claim 1, wherein said resecting step comprises resecting said cornea such that a disk of said cornea is removed from said person's eye to expose said inner layer of said cornea.

5. The method of claim 3, wherein said resecting step comprises slicing said cornea using a microkeratome to result in a corneal flap of a thin, substantially uniform thickness.

6. The method of claim 1, wherein said step of sculpting said inner corneal layer is accomplished using a VISX laser eye surgery apparatus.

7. In a LASIK vision correction surgical procedure comprising resecting at least a portion of a cornea of an eye to expose an inner corneal layer, ablating at least a portion of said exposed inner corneal layer using laser radiation from a laser beam to produce a desired topography of said inner corneal layer and repositioning said resected portion of said cornea onto the eye, an improved method of positioning and adhering said resected portion of said cornea into its original position on the eye comprising the steps of: floating the resected portion of the cornea into its original position over said ablated inner corneal layer in a sterile solution to remove debris from the eye and ensure proper flap orientation and smoothness; observing a gutter substantially circumferentially surrounding said repositioned portion of said cornea; applying filtered, compressed air at a rate of sub stantially between zero and 2.5 liters per minute to said repositioned portion of said cornea; and terminating the application said filtered, compressed air when said gutter is observed to be substantially dry.

8. In a LASIK vision correction surgical procedure, the improved method of positioning and adhering said resected portion of said cornea into its original position on the eye as claimed in claim 7, wherein said drying step is performed for substantially between 15 and 30 seconds.

9. In a LASIK vision correction surgical procedure, the improved method of positioning and adhering said resected portion of said cornea into its original position on the eye as claimed in claim 7, wherein said step of observing said gutter comprises using a microscope.

10. In a LASIK vision correction surgical procedure, the improved method of positioning and adhering said resected portion of said cornea into its original position on the eye as claimed in claim 7, wherein said step of applying filtered compressed air comprises applying said filtered compressed air using a Kawesch flap dryer.

11. An apparatus for surgical vision correction comprising:

a means for resecting at least a portion of a cornea of an eye to expose an inner layer of said cornea;

a laser apparatus for ablating said exposed inner layer of said cornea to produce a desired corneal topography;

a source of sterile solution for floating said resected portion of said cornea back into its original position on said eye;

a source of compressed air for drying said eye, said source of compressed air including volume and pressure regulators to control the flow of said compressed air; and a microscope for viewing said repositioned portion of said cornea to ensure proper orientation and smoothness and for viewing a gutter substantially circumferentially surrounding said replaced portion of said cornea while said replaced portion is being dried in its original position.

12. The apparatus claimed in claim 11, wherein said laser apparatus comprises a VISX vision system.

13. The apparatus claimed in claim 11, wherein said compressed air source further comprises a Kawesch flap dryer.

* * * * *